US011963888B2

(12) United States Patent
Seifert et al.

(10) Patent No.: US 11,963,888 B2
(45) Date of Patent: *Apr. 23, 2024

(54) METHOD FOR CONTROLLING THE STANDING-PHASE DAMPING OF AN ARTIFICIAL KNEE JOINT

(71) Applicant: OTTO BOCK HEALTHCARE PRODUCTS GMBH, Vienna (AT)

(72) Inventors: Dirk Seifert, Vienna (AT); Sven Zarling, Duderstadt (DE)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 129 days.

This patent is subject to a terminal disclaimer.

(21) Appl. No.: 17/347,202

(22) Filed: Jun. 14, 2021

(65) Prior Publication Data

US 2021/0298921 A1 Sep. 30, 2021

Related U.S. Application Data

(63) Continuation of application No. 15/568,779, filed as application No. PCT/EP2016/058394 on Apr. 15, 2016, now Pat. No. 11,033,406.

(30) Foreign Application Priority Data

Apr. 24, 2015 (DE) .................... 10 2015 106 392.1

(51) Int. Cl.
*A61F 2/70* (2006.01)
*A61F 2/50* (2006.01)
(Continued)

(52) U.S. Cl.
CPC ................ *A61F 2/50* (2013.01); *A61F 2/64* (2013.01); *A61F 2/70* (2013.01); *A61H 3/00* (2013.01);
(Continued)

(58) Field of Classification Search
CPC ...... A61F 2/64; A61F 2/68; A61F 2002/5033; A61F 2002/6818; A61F 2002/74; A61F 2002/7625; A61H 3/00
See application file for complete search history.

(56) References Cited

U.S. PATENT DOCUMENTS 5,571,205 A 11/1996 James
6,610,101 B2 8/2003 Herr et al.
(Continued)

FOREIGN PATENT DOCUMENTS

CA 2779784 A1 5/2011
CN 1074109 A 7/1993
(Continued)

OTHER PUBLICATIONS

PCT International Search Report for PCT International Patent Application No. PCT/EP2016/058394, dated Jun. 16, 2016.

*Primary Examiner* — Christie Bahena
(74) *Attorney, Agent, or Firm* — HOLLAND & HART LLP

(57) ABSTRACT

A method for controlling the standing-phase damping of an artificial knee joint comprising an upper part and a lower part which are secured together in a pivotal manner about a pivot axis, a resistance unit which is arranged between the upper part and the lower part and has an adjustment device via which the damping resistance can be modified, and a control unit which is coupled to the adjustment device and which is connected to at least one sensor. The adjustment is carried out on the basis of sensor data, and the knee angle is detected by the at least one sensor during the standing-phase inflexion up to the terminal standing phase. The flexion damping is increased to a level above an initial flexion damping in order to prevent a further inflexion upon reaching a specified maximum knee angle.

19 Claims, 2 Drawing Sheets

(51) Int. Cl.
  *A61F 2/64*  (2006.01)
  *A61F 2/68*  (2006.01)
  *A61H 3/00*  (2006.01)
  *A61F 2/74*  (2006.01)
  *A61F 2/76*  (2006.01)

(52) U.S. Cl.
  CPC ............... *A61F 2002/5004* (2013.01); *A61F 2002/5006* (2013.01); *A61F 2002/5033* (2013.01); *A61F 2002/6818* (2013.01); *A61F 2002/701* (2013.01); *A61F 2002/704* (2013.01); *A61F 2002/705* (2013.01); *A61F 2/74* (2021.08); *A61F 2002/7625* (2013.01); *A61F 2002/7635* (2013.01); *A61F 2002/764* (2013.01)

(56) References Cited

U.S. PATENT DOCUMENTS

| | | | |
|---|---|---|---|
| 7,731,759 | B2 | 6/2010 | Pusch et al. |
| 7,799,091 | B2 | 9/2010 | Herr et al. |
| 8,231,688 | B2 | 7/2012 | Fairbanks et al. |
| 10,265,198 | B2 | 4/2019 | Pusch et al. |
| 10,285,827 | B2 * | 5/2019 | Zahedi ................ A61F 2/6607 |
| 2005/0015156 | A1 | 1/2005 | Hikichi |
| 2009/0054996 | A1 | 2/2009 | Sykes et al. |
| 2009/0171468 | A1 | 7/2009 | Pusch et al. |
| 2009/0192619 | A1 | 7/2009 | Martin et al. |
| 2009/0265018 | A1 | 10/2009 | Goldfarb et al. |
| 2010/0023133 | A1 | 1/2010 | Fairbanks et al. |
| 2010/0049334 | A1 | 2/2010 | Okuda et al. |
| 2010/0305716 | A1 | 12/2010 | Pusch et al. |
| 2011/0087339 | A1 | 4/2011 | Pusch et al. |
| 2012/0215323 | A1 | 8/2012 | Seyr et al. |
| 2012/0226364 | A1 | 9/2012 | Kampas et al. |
| 2012/0226365 | A1 | 9/2012 | Seyr et al. |
| 2012/0232674 | A1 | 9/2012 | Kampas et al. |
| 2013/0310949 | A1 | 11/2013 | Goldfarb et al. |
| 2014/0379096 | A1 | 12/2014 | Zahedi et al. |
| 2015/0018972 | A1 | 1/2015 | Albrecht-Laatsch |
| 2015/0164660 | A1 | 6/2015 | Will et al. |
| 2016/0206447 | A1 | 7/2016 | Auberger et al. |

FOREIGN PATENT DOCUMENTS

| | | |
|---|---|---|
| CN | 1431888 A | 7/2003 |
| CN | 101453963 A | 6/2009 |
| CN | 101961271 A1 | 2/2011 |
| CN | 102065799 A | 5/2011 |
| CN | 102740803 A | 10/2012 |
| CN | 103271783 A | 9/2013 |
| DE | 102006021802 A1 | 11/2007 |
| DE | 102007053389 A1 | 5/2009 |
| DE | 102008008284 A1 | 8/2009 |
| DE | 102009052887 A1 | 5/2011 |
| DE | 102009052890 A1 | 5/2011 |
| DE | 102009052895 A1 | 5/2011 |
| DE | 102012003369 A1 | 8/2013 |
| DE | 102012013141 A1 | 5/2014 |
| JP | 2009/536050 | 10/2009 |
| RU | 2254832 C1 | 6/2005 |
| WO | 01/72245 A2 | 10/2001 |
| WO | 2007/128299 A1 | 11/2007 |
| WO | 2009/059594 A2 | 5/2009 |
| WO | 2009/097841 A1 | 8/2009 |
| WO | 2010/005473 A1 | 1/2010 |
| WO | 2011/057791 A1 | 5/2011 |
| WO | 2011/057792 A1 | 5/2011 |
| WO | 2011/057795 A1 | 5/2011 |
| WO | 2013/124071 A1 | 8/2013 |
| WO | 2014/005679 A2 | 1/2014 |

* cited by examiner

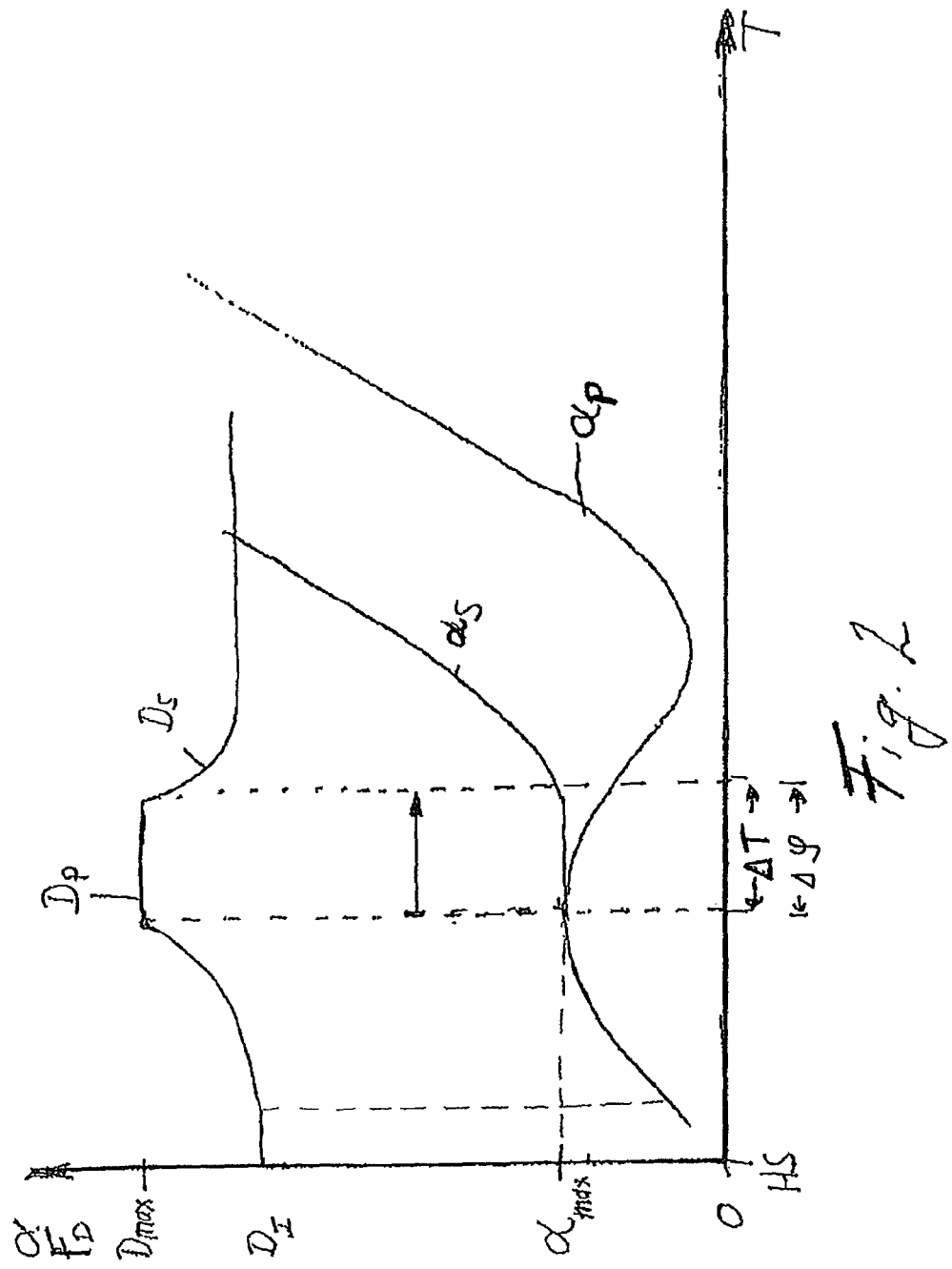

METHOD FOR CONTROLLING THE STANDING-PHASE DAMPING OF AN ARTIFICIAL KNEE JOINT

CROSS-REFERENCE TO RELATED APPLICATIONS

This is a continuation application of U.S. patent application Ser. No. 15/568,779, filed Oct. 23, 2017, and entitled METHOD FOR CONTROLLING THE STANDING-PHASE DAMPING OF AN ARTIFICIAL KNEE JOINT, pending, which is a U.S. National Entry Application from International Patent Application No. PCT/EP2016/058394, filed Apr. 15, 2016, and also entitled METHOD FOR CONTROLLING THE STANDING-PHASE DAMPING OF AN ARTIFICIAL KNEE JOINT, which claims the benefit of German Patent Application No. 102015106392.1, filed Apr. 24, 2015, the disclosures of which are incorporated, in their entireties, by this reference.

TECHNICAL FIELD

The invention relates to a method for controlling the stance phase damping of an artificial knee joint having an upper part and a lower part which are fastened to one another in a manner pivotable about a pivot axis and having a resistance unit which is arranged between the upper part and the lower part and which has an adjustment device by means of which the damping resistance can be modified, having a control unit which is coupled to the adjustment device and which is connected at least to a sensor, wherein the adjustment is carried out on the basis of sensor data.

BACKGROUND

Knee joints for orthoses, exoskeletons or prostheses have an upper part with an upper connection part and a lower part with a lower connection part, which are articulatedly connected to one another. In general, receptacles for a thigh stump or a thigh rail are arranged on the upper connection part, whereas a lower leg tube or a lower leg rail are arranged on the lower connection part. In the simplest case, the upper part and the lower part are connected pivotably to one another by means of a uniaxial joint.

To be able to satisfy or support different requirements during the different phases of a step or during other movements or actions in a way that is as natural as possible, a resistance device is often provided which provides flexion resistance and extension resistance. The flexion resistance is used for setting how easily the lower part can be swung backwards in relation to the upper part when a force is applied. The extension resistance brakes the forward movement of the lower part and forms, inter alia, an extension limit stop.

DE 10 2008 008 284 A1 has disclosed an orthopedic knee joint with an upper part and with a lower part arranged pivotably thereon, which lower part is assigned multiple sensors, for example a flexion angle sensor, an acceleration sensor, an inclination sensor and/or a force sensor. The position of the extension stop is determined in a manner dependent on the sensor data.

DE 10 2006 021 802 A1 describes control of a passive prosthetic knee joint with adjustable damping in a flexion direction for adaptation of a prosthesis device with top-side connection means and with a connecting element to an artificial foot. The adaptation is made to climbing stairs, wherein a low-moment lifting of the prosthetic foot is detected, and the flexion damping is, in a lifting phase, lowered to below a level suitable for walking on a level surface. The flexion damping may be increased in a manner dependent on the change in the knee angle and in a manner dependent on the axial force acting on the lower leg.

DE 10 2009 052 887 A1 describes, inter alia, a method for controlling an orthotic or prosthetic joint with a resistance device and with sensors, wherein items of state information are provided by means of sensors during the use of the joint. The sensors detect moments or forces, wherein the sensor data of at least two of the determined variables are linked to one another by means of a mathematical operation, and in this way an auxiliary variable is calculated which is used as a basis for the control of the flexion and/or extension resistance.

According to the prior art, for the control of the change in the damping behavior, the sensor data are evaluated quantitatively, that is to say, in general, certain threshold values are predefined, in the case of the attainment or non-attainment of which the actuator is activated or deactivated, such that the resistance device provides an increased or reduced flexion or extension resistance.

Patients may use prostheses, exoskeletons or orthoses in various environments. They may walk down stairs, walk down ramps or walk on a level surface at various speeds. Furthermore, loads may be carried, which likewise has an effect on the behavior of the prosthesis or orthosis. In particular after the end of the swing phase, that is to say after the setting-down of the aided leg, when the body weight is shifted onto the aided leg, there is often a requirement for increased safety for the patient. Excessively high initial flexion damping, that is to say damping which counteracts flexion of the artificial knee joint, would however lead to a shock load in the hip joint, which would result in a reduction in wearing comfort and acceptance of the prosthesis or orthosis.

SUMMARY

It is an object of the present invention to provide a method for controlling an artificial knee joint, in particular the variation of the damping within an artificial knee joint, with which adaptation to different walking situations and comfortable walking behavior can be achieved with simultaneously maximum safety.

According to the invention, said object is achieved by means of a method having the features of the main claim. Advantageous embodiments and refinements of the invention are disclosed in the subclaims, in the description and in the figures.

The method for controlling the stance phase damping of an artificial knee joint having an upper part and a lower part which are fastened to one another in a manner pivotable about a pivot axis and having a resistance unit which is arranged between the upper part and the lower part and which has an adjustment device by means of which the damping resistance can be modified, having a control unit which is coupled to the adjustment device and which is connected at least to a sensor, wherein the adjustment is carried out on the basis of sensor data, provides that, during the stance phase flexion up until the terminal stance phase, the knee angle is detected by means of the at least one sensor, and the flexion damping is increased to a level above an initial flexion damping, to the point of prevention of further flexion when a set maximum knee angle is reached. After the end of the swing phase, the damping resistance, significant is the flexion resistance, is set to a level suitable for providing sufficient damping in the event of a heel strike. The level is then the level of an initial flexion damping. During the further course of the stance phase, the knee angle increases, because a ground reaction force builds up in the manner of a pulse as a result of the heel strike, and a torque about the pivot axis is effected owing to the introduction of force together with a forward movement of the body. An unaided leg will cushion the heel strike owing to muscle contractions; in the case of an aided leg, this is effected by the resistance unit with the initial flexion damping. Upon the initial ground contact or heel strike, a flexion angle or knee angle of approximately 5° is reached. During the next movement phase, the loading response, the load on the leg is intensified by the body weight, which leads to a further flexion or destabilization of the knee joint. An unaided leg would absorb a further flexion by tensing of the leg extensor muscles. According to the invention, it is provided that, after the initial ground contact or heel strike the flexion damping is increased to a level above the initial flexion damping, which level is sufficient to prevent further flexion when a set maximum knee angle is reached. The maximum attainable knee angle is set in advance; when walking on ramps or on a level surface, the maximum knee angle lies in a range between 7° and 12°. The variation of the flexion damping is thus performed such that, with increasing knee angle, wherein a fully extended position has the knee angle of 0°, the flexion damping is monitored as regards whether and how the knee angle increases. If the knee angle approaches the set maximum knee angle, the flexion damping is increased; a progressive increase is preferably performed, that is to say initially a slow increase of the flexion damping, before the flexion damping is then, shortly before the set maximum knee angle is reached, increased to such an extent that further flexion cannot occur, that is to say a flexion stop is effected. The resistance unit, which may be designed for example as a hydraulic, pneumatic, electrical or mechanical resistance unit or brake, is blocked. In the case of hydraulic or pneumatic resistance units, flow transfer channels are closed, such that no further medium can flow from an extension chamber into a flexion chamber. In the case of mechanical resistance devices, it is for example the case that the friction is increased to such an extent that no further flexion can occur; the same applies to electrically actuated resistance units. The method is provided for the control both of prostheses and of orthoses and exoskeletons. Where orthoses are referred to below, the statements likewise apply to the special form of the orthosis in the form of an exoskeleton. The sensor or the sensors detect(s) the measurement variables over the entire stance phase, from the moment of initial contact of the foot or foot part with the ground, the initial ground contact or heel strike, up until the terminal stance phase, in which full extension of the knee joint is reached and the knee joint is held in the extended position by means of a resistance to a dorsal extension and the position of the force vector in front of the knee axis. After the terminal stance phase, in the so-called pre-swing phase, preparation for the swing phase is performed; in the case of a healthy leg, passive flexion of the knee joint commences, but the toes have not yet lifted off from the ground.

One refinement of the invention provides that the flexion damping is held at the level present when the maximum knee angle is reached. In this way, an increased level of safety is provided, such that the artificial knee joint does not collapse during the further course of walking. When walking on a level surface, a relative maximum is followed by a decrease in the knee angle, that is to say an extension, which continues up until the terminal stance phase. In this phase, the knee angle decreases to a point of full extension. The maintaining of the flexion damping at the level of the maximum knee angle during the loading response thus yields an increase in safety without an adverse effect on walking on a level surface.

The flexion damping may be held constant during the initial heel strike and increased in a manner dependent on the loading. The increase is advantageously performed only after the so-called loading response is reached, a phase of walking in which the foot is in full contact with the ground and the force vector moves, after the initial heel strike, behind the knee axis, whereby the knee flexion is effected and, in the case of a healthy leg, the forward thigh muscle is activated in order to slow the flexion. In the case of the artificial knee joint, the flexion damping is increased in a manner dependent on the loading the flexion damping after the heel strike, and is increased more in the case of a high loading than in the case of a low loading.

A refinement of the invention provides that a forward rotation of the lower part, that is to say of the lower leg tube in the case of a prosthesis or a lower leg rail in the case of an orthosis, about a distal center of rotation is detected, preferably is detected by means of sensors. The movement of the lower leg about the ankle joint or about an imaginary center of rotation in the ground region is determined or detected in order that conclusions can be drawn regarding the further movement behavior. In the case of a continued forward rotation after the maximum knee angle is reached, the flexion damping may then be decreased in order that, during the terminal stance phase or the pre-swing phase, sufficiently easy flexion of the knee joint is permitted in order that a toe lift-off can occur easily. A continued forward rotation may occur even without a decrease of the knee angle for example when walking down ramps and stairs, if a further forward rotation of the lower part occurs as a result of the further rolling movement about the heel or about the center of rotation on an edge of a step, which may be detected for example by means of a separate sensor, for example an inertial angle sensor. Said sensor is also connected to the control unit, which is coupled to the adjustment device and adapts the flexion resistance.

The flexion damping may be decreased after an overshooting of a set range of the forward rotation and/or in the case of a decreasing knee angle. The range of the forward rotation may for example encompass a set angle range through which the lower part must perform a forward rotation about a distal center of rotation. If for example a forward rotation of 5° to 10° is detected, the controller assumes that, either in the case of walking on a level surface or in the case of alternating walking down ramps and/or stairs, a further forward movement has occurred and a decrease of the flexion damping is necessary. The decrease of the flexion damping on the basis of the monitoring of a set range of a forward rotation may be used separately or in combination with the detection of a decreasing knee angle.

The flexion damping may, after the setting of the maximum flexion damping of the initial stance phase, be decreased to a value greater than or equal to the initial stance phase flexion damping. In this way, for example when walking down ramps or stairs, an increased level of safety against undesired flexion is provided.

One refinement of the invention provides that the flexion damping is decreased after a set maximum knee angle is reached and after a forward rotation of the lower part. If, when walking, in particular when walking down ramps or inclined surfaces, the maximum knee angle determined or predefined for the patient is reached, and if a forward rotation of the lower part also occurs, which is detected for example by means of an inertial angle sensor or an ankle joint angle sensor, it is the case according to the invention that the flexion resistance is decreased in order to provide further flexion of the knee joint and thus uniform walking and a natural gait pattern.

The maximum knee angle may be selected and set from a range between 7° and 12° or from a range between 11° and 9°; a common value for maximum knee angles is 10°. This is approximately half of the knee angle attained by an unaided leg as flexion during the loading response.

The maximum knee angle may also be set on the basis of statistical evaluations of detected knee angles for walking on a level surface, wherein the statistical evaluations may be performed in the control unit of the artificial knee joint. It is thereby made possible for the maximum knee angle to be individually set for the respective user of the artificial knee joint.

The method is suitable for the control of the stance phase damping in particular when walking on a level surface and when walking down ramps; the special situation of walking down stairs requires different control.

The resistance unit may for example be configured as an actuator, for example as a hydraulic, pneumatic, magnetorheological, magnetic, electrical, mechanical or electromagnetic resistance unit. In the case of hydraulic or pneumatic resistance units, flow transfer channels are closed, such that said flow transfer channels can no longer allow medium to flow from an extension chamber into a flexion chamber. In this way, the flow of the medium between the extension chamber and the flexion chamber can possibly also be prevented entirely. In the case of mechanical resistance devices, it is for example the case that the friction is increased to such an extent that no further flexion is possible. The same applies to electrically actuated resistance units.

Use may also be made of actuators which both actively introduce energy into the system and also conversely extract energy from the system, and thereby act as a resistance unit. Actuators may for example be formed as electric motors, hydraulic or pneumatic pumps or piezoelectric elements.

BRIEF DESCRIPTION OF THE DRAWINGS

An exemplary embodiment of the invention will be discussed in more detail below on the basis of the appended figures. In the figures:

FIG. 2—shows an illustration of a control diagram.

DETAILED DESCRIPTION

Figure 1:
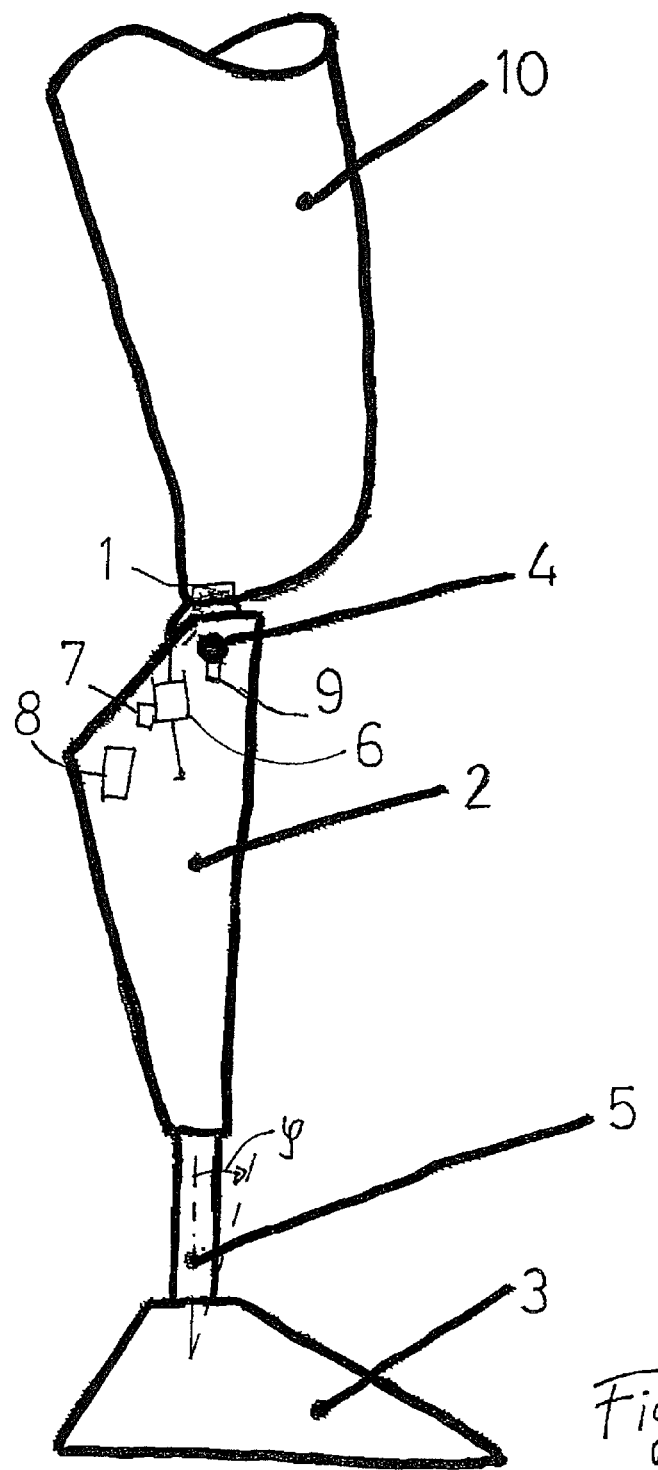
FIG. 1—shows a schematic illustration of a leg prosthesis.

FIG. 1 shows, in a schematic illustration, a leg prosthesis with an upper part 1 to which a thigh socket 10 for receiving a thigh stump is fastened. A lower part 2 designed as a lower leg part is arranged pivotably on the upper part 1. The lower part 2 is mounted on the upper part 1 pivotably about a pivot axis 4. The lower part 2 has a lower leg tube 5, to the distal end of which there is fastened a prosthetic foot 3 in which there may be accommodated a device for determining the axial force acting on the lower leg tube 5 and the ankle moment acting about the fastening point of the prosthetic foot 3 to the lower leg tube 5.

In or on the lower part 2 there is arranged a resistance device 6 which may be formed for example as a damper or actuator and which is supported between the upper part 1 and the lower part 2 in order to provide an adjustable extension resistance and flexion resistance. The resistance device 6 is assigned an adjustment device 7, for example a motor, a magnet or some other actuator, by means of which the respective resistance R within the resistance device 6 can be varied. If the resistance device 6 is formed as a hydraulic damper or pneumatic damper, it is possible by means of the adjustment device 7 for the respective flow cross section of a flow transfer channel to be increased or decreased in size. It is likewise possible for the flow resistance to be varied in some other way by means of the adjustment device 7. This may be realized for example by opening or closing valves or changing viscosities or magnetorheological characteristics. If the resistance device is formed as an electric motor operating as a generator, it is possible for an increase or decrease in the respective resistances to flexion or extension to be set through variation of the electrical resistance.

To be able to activate or deactivate the adjustment device 7, a control device 8 is assigned to the lower part 2, in particular is accommodated in a lower leg trim, by means of which control device a corresponding activation or deactivation signal is output to the adjustment device 7. The adjustment device 7 is activated or deactivated on the basis of sensor data, and the sensor data are provided by one or more sensors 9 which are arranged on the artificial knee joint. These may be angle sensors, acceleration sensors and/or force sensors. The sensors 9 are connected to the control device 8, for example by cable or by means of a wireless transmission device. In the exemplary embodiment illustrated, the sensor 9 is formed inter alia as a knee angle sensor.

The entire step cycle from the heel strike to the new, next heel strike HS, and thus also the entire swing phase with the swing phase extension and the swing phase flexion, is monitored by means of the sensors 9.

In FIG. 2, the knee angle $\alpha$ and the flexion damping $F_D$ are plotted versus the time in a diagram. The knee angle $\alpha$ is depicted for two walking situations from the start of the stance phase, that is to say from the heel strike HS, up until the terminal stance phase. The lower curve profile $\alpha_P$ shows the knee angle profile for walking on a level surface, and the upper curve profile $\alpha_S$ shows the knee angle profile for walking down a ramp or stairs, wherein the illustration here relates to the aided leg in the case of alternating walking.

The normal knee angle profile for walking on a level surface as per curve $\alpha_P$ begins at a fully extended position in the region of the heel strike HS, leads, after the initial ground contact, to an increase of the knee angle $\alpha$ up to a local maximum $\alpha_{max}$ at the end of the loading response, before then decreasing again during the middle stance phase. The leg is then in an approximately extended position; during the further course of the step, the knee angle $\alpha$ increases again in the region of the terminal stance phase and pre-swing phase.

The knee angle profile for alternating walking down ramps, as illustrated in curve as, has no decrease at the end of the loading response, with the artificial knee joint rather remaining at a constant value $\alpha_{max}$ until it is then flexed further earlier than in the case of walking on a level surface.

To provide reliable damping behavior for the stance phase flexion for both gait patterns, the damping resistance $F_D$ or flexion resistance is initially set to an initial damping level $F_{DI}$ which permits flexion of the artificial knee joint upon the initial ground contact but dampens and brakes the flexion in order to prevent a collapse of the artificial knee joint. Said initial flexion damping $F_{DI}$ is initially maintained at a constant level until the knee angle $\alpha$ has reached a threshold value. In the exemplary embodiment illustrated, the threshold value amounts to approximately 30% of the set maximum knee angle $\alpha_{max}$ that is admissible or considered to be admissible; the increase of the flexion damping $F_D$ begins almost directly after the heel strike. Alternatively, the threshold value may also lie at a greater knee angle, for example at 50% or 70% of the set maximum knee angle $\alpha_{max}$ that is admissible or considered to be admissible. When the set threshold value for the knee angle $\alpha$ is reached, the flexion damping $F_D$ is increased in order to brake the further flexion of the knee joint and block said flexion when the maximum knee angle $\alpha_{max}$ is reached. In the illustrated exemplary embodiment, the flexion damping is increased progressively, though it may also be increased degressively or linearly. When the maximum knee angle $\alpha_{max}$ is reached, the flexion damping $F_D$ is at the maximum flexion damping value $F_{Dmax}$, at which further flexion is no longer possible. Said resistance value $F_{Dmax}$ is held over a set time period $\Delta T$; a plateau $D_P$ of the maximum flexion resistance $F_{Dmax}$ forms, and no flexion of the artificial knee joint is possible during said time.

The time period $\Delta T$ for which said level $F_{Dmax}$ is held is detected either by means of a timing switching element or by means of the detection of a forward rotation $\Delta \varphi$ of the lower part 2, for example of the lower leg tube 5, or a pivoting movement about the ankle joint of the prosthetic foot 3. If a further forward rotation by the angle $\varphi$ occurs, which can be detected by means of acceleration sensors, angle sensors and/or inertial angle sensors, the user of the artificial knee joint moves further forward. A possible angle range for a further forward rotation $\varphi$ can be assumed to be pivot angles of 5° to 10°. After the threshold value for the further forward rotation is reached or the time elapses, the flexion damping $F_{Dmax}$ is decreased. In the exemplary embodiment illustrated, the decrease is degressive, such that initially a rapid decrease of the flexion damping is effected, for example in order to permit a further flexion when walking down a ramp, as shown by the profile of the curve $\alpha_S$. Other profiles of the decrease in damping may be set, for example progressively or linearly. In the plateau region with the resistance plateau $D_P$ during the time $\Delta T$, no further flexion movement of the artificial knee joint occurs. Only after the flexion resistance $F_D$ decreases to a level below the maximum flexion resistance $F_{Dmax}$, in the illustrated exemplary embodiment above a level of the initial flexion damping $F_{DI}$ in the region of the decrease curve $F_{DS}$, is an increasing flexion made possible.

The advantage of such control lies in the high level of safety, which is based on an initial knee flexion always limited to the maximum knee angle $\alpha_{max}$, without the extent of movement or the functionality during the further movement sequence being restricted here. If the maximum knee angle $\alpha_{max}$ is reached and the leg rotates further forward without knee extension occurring, as shown in the curve as, the flexion damping $F_D$ is reduced in continuous fashion to a high level of damping, possibly to the initial flexion damping $F_{DI}$. Thus, when walking down ramps or stairs, it is ensured, without any loss of safety, that an undisrupted further movement sequence is possible.

The invention claimed is:

1. A method for controlling the stance phase damping of an artificial knee joint, the method comprising:
    providing an upper part and a lower part which are fastened to one another in a manner pivotable about a pivot axis, a resistance unit which is arranged between the upper part and the lower part and which has an adjustment device to modify the damping resistance, a control unit which is coupled to the adjustment device and which is connected to at least one sensor, wherein the adjustment is carried out using sensor data from the at least one sensor;
    detecting, during a period from an initial heel strike of a stance phase up until a terminal stance phase, a knee angle using the at least one sensor;
    holding a flexion damping constant at an initial flexion damping value from an initial heel strike until the knee angle has reached a threshold value;
    increasing the flexion damping in a manner dependent on load to a level above the initial flexion damping value from when the knee angle has reached the threshold value until the knee angle has reached a set maximum knee angle; and
    holding the flexion damping constant at the level above the initial flexion damping value from when the knee angle has reached the set maximum knee angle until either a set period of time has elapsed or a forward rotation of the lower part is detected, wherein when the knee angle has reached the set maximum knee angle further flexion is prevented until either the set period of time has elapsed or the forward rotation of the lower part is detected.

2. The method as claimed in claim 1, wherein a forward rotation of the lower part about a distal center of rotation is detected and, in the case of the continued forward rotation after the maximum knee angle is reached, the flexion damping is decreased.

3. The method as claimed in claim 2 wherein the flexion damping is decreased to a value greater than or equal to the initial stance phase flexion damping.

4. The method as claimed in claim 1, wherein the flexion damping is decreased after an overshooting of a set range of a forward rotation and a decreasing knee angle.

5. The method as claimed in claim 1, wherein the flexion damping is decreased after a set maximum knee angle is reached and after a relative forward rotation of the lower part about an ankle joint or about a center of rotation in a ground region.

6. The method as claimed in claim 1, wherein the maximum knee angle is selected and set from a range between 7° and 12° or from a range between 9° and 11°.

7. The method as claimed in claim 1, wherein the maximum knee angle is defined using statistical evaluations of detected knee angles for walking on a level surface.

8. The method as claimed in claim 1, wherein the maximum knee angle is individually set for a respective user of the artificial knee joint.

9. The method as claimed in claim 1, wherein the detecting occurs between heel strike and terminal stance phase at a point when the lower part is fully extended and the knee angle is zero.

10. The method as claimed in claim 1, wherein the flexion damping is increased after a foot is in full contact with a ground.

11. A method to control the stance phase damping of an artificial knee joint, the method comprising:
    providing an upper part, a lower part, a resistance unit, a control unit, and at least one sensor coupled to the control unit, the upper and lower parts being pivotally connected to each other, the resistance unit having an adjustment device and being operable to modify a damping resistance of the artificial knee joint, and the control unit is coupled to the adjustment device to control adjustments to the damping resistance based on sensor data from the at least one sensor;

detecting a knee angle with the at least one sensor during a period from an initial heel strike of a stance phase up to a terminal stance phase;

holding a flexion damping constant at an initial flexion damping value from an initial heel strike until the knee angle has reached a threshold value;

increasing the flexion damping in a manner dependent on load to a level above the initial flexion damping value from when the knee angle has reached the threshold value until the knee angle has reached a set maximum knee angle; and holding the flexion damping constant at the level above the initial flexion damping value from when the knee angle has reached the set maximum knee angle until either a set period of time has elapsed or a forward rotation of the lower part is detected, wherein when the knee angle has reached the set maximum knee angle further flexion is prevented until either the set period of time has elapsed or the forward rotation of the lower part is detected.

12. The method as claimed in claim 11, further comprising detecting the forward rotation of the lower part about a distal center of rotation and decreasing the flexion damping after the maximum knee angle is reached during a continued forward rotation.

13. The method as claimed in claim 11, further comprising decreasing the flexion damping after detecting an overshooting of a set range of a forward rotation and a decreasing knee angle.

14. The method as claimed in claim 13, further comprising decreasing the flexion damping to a value greater than or equal to the initial stance phase flexion damping.

15. The method as claimed in claim 11, further comprising decreasing the flexion damping after reaching a set maximum knee angle and after a relative forward rotation of the lower part about an ankle joint or about a center of rotation in a ground region.

16. The method as claimed in claim 11, wherein the maximum knee angle is selected and set from a range between 7° and 12° or from a range between 9° and 11°.

17. The method as claimed in claim 11, wherein the maximum knee angle is defined using statistical evaluations of detected knee angles for walking on a level surface.

18. The method as claimed in claim 11, wherein the maximum knee angle is individually set for a respective user of the artificial knee joint.

19. The method as claimed in claim 11, wherein the detecting occurs between heel strike and terminal stance phase at a point when the lower part is fully extended and the knee angle is zero.

* * * * *